United States Patent
Chapusot

(10) Patent No.: US 9,492,088 B2
(45) Date of Patent: Nov. 15, 2016

(54) MEDICAL DEVICE FOR THE MEASUREMENT AND PROCESSING OF A HEALTH PARAMETER OF A PATIENT

(71) Applicant: WELCOOP PHARMA, Vandoevre les Nancy (FR)

(72) Inventor: Thierry Chapusot, Messein (FR)

(73) Assignee: MARQUE VERTE SANTE, Vandoeuvre les Nancy (FR)

( * ) Notice: Subject to any disclaimer, the term of this patent is extended or adjusted under 35 U.S.C. 154(b) by 94 days.

(21) Appl. No.: 14/389,872

(22) PCT Filed: Apr. 11, 2013

(86) PCT No.: PCT/FR2013/050784
§ 371 (c)(1),
(2) Date: Oct. 1, 2014

(87) PCT Pub. No.: WO2013/153334
PCT Pub. Date: Oct. 17, 2013

(65) Prior Publication Data
US 2015/0048956 A1    Feb. 19, 2015

(30) Foreign Application Priority Data

Apr. 12, 2012 (FR) ................................ 12 53359

(51) Int. Cl.
*A61B 5/00* (2006.01)
*A61B 5/0205* (2006.01)
(Continued)

(52) U.S. Cl.
CPC ......... *A61B 5/0022* (2013.01); *A61B 5/02055* (2013.01); *A61B 5/1172* (2013.01); *A61B 5/1176* (2013.01); *A61B 5/14532* (2013.01); *A61B 5/14546* (2013.01); *A61B 5/742* (2013.01); *G06F 21/32* (2013.01);
(Continued)

(58) Field of Classification Search
CPC .......................... A61B 5/02438; A61B 5/0002
See application file for complete search history.

(56) References Cited

U.S. PATENT DOCUMENTS

| | | | |
|---|---|---|---|
| 7,683,759 B2 * | 3/2010 | Martis | A61B 3/005 340/5.74 |
| 7,887,345 B2 * | 2/2011 | Wong | A61B 5/14552 439/140 |

(Continued)

*Primary Examiner* — Jennifer Mehmood
*Assistant Examiner* — Rufus Point
(74) *Attorney, Agent, or Firm* — Andrew W. Chu; Craft Chu PLLC

(57) ABSTRACT

The invention concerns a medical device comprising a device for the measurement of a health parameter of a patient, a device for capturing a fingerprint identifying the patient, a device for communicating with a remote server and a control means, the control means being designed such that, when it is activated by a single action of the patient, it: activates the device for the measurement of a health parameter of the patient, and obtains a measured parameter in return, activates the fingerprint capture device and obtains a fingerprint in return, and then provides the measured parameter and the captured fingerprint to the communication device in order to transmit the measured parameter and the captured fingerprint to the remote server.

12 Claims, 1 Drawing Sheet

(51) Int. Cl.
  *A61B 5/117* (2016.01)
  *G06F 21/32* (2013.01)
  *A61B 5/145* (2006.01)
  *A61B 5/024* (2006.01)
  *A61B 5/021* (2006.01)
  *G07C 9/00* (2006.01)

(52) U.S. Cl.
  CPC ............... *A61B 5/021* (2013.01); *A61B 5/024* (2013.01); *A61B 5/02438* (2013.01); *A61B 2560/0266* (2013.01); *G07C 9/00158* (2013.01)

(56) References Cited

U.S. PATENT DOCUMENTS

| | | | |
|---|---|---|---|
| 8,073,518 B2* | 12/2011 | Chin | A61B 5/14552 600/310 |
| 8,649,839 B2* | 2/2014 | Chin | A61B 5/14552 600/324 |
| 8,679,012 B1* | 3/2014 | Kayyali | A61B 5/0002 382/115 |
| 9,250,104 B2* | 2/2016 | Greiner | A61B 5/0006 |
| 2005/0102167 A1* | 5/2005 | Kapoor | A61B 5/0006 705/3 |
| 2006/0074280 A1* | 4/2006 | Martis | A61B 3/005 600/310 |
| 2006/0075257 A1* | 4/2006 | Martis | A61B 3/005 713/186 |
| 2007/0100221 A1* | 5/2007 | Sato | A61B 5/14552 600/323 |
| 2009/0043180 A1* | 2/2009 | Tschautscher | A61B 5/1172 600/323 |
| 2010/0182126 A1* | 7/2010 | Martis | A61B 5/1172 340/5.83 |
| 2012/0079579 A1* | 3/2012 | Kamakura | H04L 63/0861 726/7 |
| 2012/0110054 A1* | 5/2012 | Katsuki | A61B 5/0002 709/201 |
| 2012/0165614 A1* | 6/2012 | Strickland | H04L 63/08 600/300 |
| 2012/0229299 A1* | 9/2012 | Skoldengen | A61N 1/37276 340/870.02 |
| 2013/0278414 A1* | 10/2013 | Sprigg | G08B 21/0453 340/539.12 |
| 2013/0346108 A1* | 12/2013 | Kamen | G06F 19/3468 705/3 |

* cited by examiner

MEDICAL DEVICE FOR THE MEASUREMENT AND PROCESSING OF A HEALTH PARAMETER OF A PATIENT

TECHNICAL FIELD AND STATE OF THE ART

The invention relates to a medical device for remote measurement and processing of a health parameter of a patient. The invention permits the remote health monitoring of a patient.

Portable medical devices are already commercially available, which are easy to be used for measuring a health parameter of the patient. These devices comprise namely a device for measuring a parameter, for example a temperature, a blood pressure, etc., and a device for displaying the result of the measurement. These devices permit a patient to measure himself some health parameters and to monitor the evolution of his health parameters; they also permit the patient to inform his physician of the results of measurements being performed. Some of these devices also include means for transmitting the result of the measurement to a remote server, which the physician can have access to.

One difficulty of these devices is securing the data of the patient and, for the physician, the need to ensure the identity of the patient, whom the measurements were performed on.

Some of the existing medical devices have limited access: in order to activate the device, a user must provide a username, a password, etc. But once the device has been activated, any person can use the device, so that nothing guarantees that the person, whom the parameter measurements are performed on, is the one associated with the password. Moreover, such devices are necessarily aimed at being used by one single person, since one single username, one single password, etc. permits the activation of the device.

The aim of the invention is to cope with all or part of the drawbacks of the existing medical devices.

DESCRIPTION OF THE INVENTION

The invention provides a novel medical device comprising a device for measuring a health parameter of a patient, a device for capturing an imprint identifying the patient, a device for communicating with a remote server and a control means. The control means being adapted, when it is activated by a single action of the patient, for:
  activating the device for measuring a health parameter of the patient, and obtaining in return a measured parameter,
  activating a device for capturing an imprint and obtaining in return an imprint being captured that identifies the patient.
  providing the measured parameter and the captured imprint to the communication device for transmitting the measured parameter and the captured imprint to the remote server.

The medical device according to the invention thus permits the measurement of a health parameter of the patient, the capturing of an imprint of the patient, whom the measurement is performed on, and then especially to send together to a remote server the measured parameter and the captured imprint, all upon a single action by the patient. This permits to guarantee the identity of the person, whom the measurement has been performed on. Moreover, insofar as an imprint is captured systematically at every new use of the medical device, one and the same medical device can be used by different people, and it is not necessary to store in the medical device the imprint of the patient, nor a username or password. Thus, the medical device according to the invention cannot be used to fraudulently access confidential information of a patient. Moreover, the use of the medical device according to the invention is very simple for the patient, because the use of the medical device, up to and including the transmission of the results to the remote server, is fully automatic, the patient intervening only to activate the control means.

The capturing of the imprint of the patient can be performed before, simultaneously with or after the measurement of the health parameter, the important thing being that:
  the measurement device and the device for capturing an imprint are activated by one single action by the patient, in order to ensure that the measured parameter and the captured imprint correspond to the same patient,
  the measured parameter and the captured imprint are available together at the time of transmission to the remote server for further simultaneous processing.

Preferably, the device for measuring and the device for capturing an imprint are activated simultaneously, or almost simultaneously, by the control device, for example with less than five seconds (and preferably less than one second) between the activation of the device for measuring and the activation of the device for capturing an imprint. In these circumstances, it is physically not possible that the imprint being captured by the device for capturing an imprint belongs to a person other than the person, whom the measuring device acts on.

Upon receipt of a transmission, the remote server can namely:
  based on the captured imprint, identify a patient referenced in a database of patients, or issue a warning signal if the patient is not referenced,
  based on the measured parameter, validate that said parameter is within the range of expected values for the patient being identified or, if not, issue a warning signal.

The validation signals or warning signals can then be transmitted to an identified person (doctor, nurse, relative, etc.) for proper treatment (visit to the patient, proposal of appointment to the patient, etc.).

According to variants, in the case of the medical device according to the invention, the device for measuring a health parameter is for example, but non-restrictively:
  a device for measuring the weight of the patient, and/or
  a device for measuring the blood pressure of the patient, and/or
  a device for measuring a level of creatinine in the blood of the patient, and/or
  a device for measuring a level of blood glucose in the blood of the patient, and/or
  a device for measuring a level of prothrombin in the blood of the patient, and/or
  a device for measuring a temperature of the patient, and/or
  a device for measuring a heart rate of the patient.

Of course, this list of measuring devices is not exhaustive. More generally, the measurement device of the medical device according to the invention can be any measuring device known nowadays or likely to be developed in the future, capable of measuring a health parameter of a patient.

Of course, a medical device according to the invention can comprise several measuring devices; in this case, the control means preferably adapted, when activated by the patient, for:

activating devices for measuring a health parameter of the patient, successively or simultaneously, and obtaining in return a measured parameter from at least some of the measuring devices, activating the device for capturing an imprint obtaining in return an imprint that has been captured, then, supplying the measured parameters and the imprint that has been captured to the communication device for transmission to the remote server.

The device for capturing an imprint is, for example, a device for capturing a fingerprint, means for capturing an imprint of an eye, means for capturing an imprint of a face of the patient, etc. Such imprints permit to identify a person in a unique way.

In an embodiment being contemplated, the means for capturing an imprint is a device for capturing a fingerprint, comprising a touch screen arranged so to activate the control means when the presence of a finger is detected on the touch screen, and copying means arranged so as to capture an image of an imprint of a finger into contact with the touch screen when the copying means is activated by the control means. The advantage of this embodiment is that the activation of the control means and capturing of an imprint occur simultaneously or almost simultaneously: at one single application of the finger of the patient on the touch screen, the touch screen activates the control means, the control means activates the copying means and obtains in return an image of an imprint of the finger resting on the touch screen. The use of the medical device according to the invention is thus very easy for the patient, because the use of the medical device, up to and including the transmission of the results to the remote server is fully automatic, the patient intervening only to activate the control means. Another advantage of a device for capturing a fingerprint: such a device is nowadays widespread, reliable, efficient and inexpensive.

According to an embodiment, the communication device can comprise a device for storing a parameter for connection to a communication network such as a telephone network or a network such as Internet, and a transmission device, and the control means is also adapted for:

reading from the storage device a connection parameter and providing the connection parameter and a connection request to the transmission device, which transmits to the communication network, associating the measured parameter and the captured imprint in one single message and providing the single message to the transmission device, which transmits to the server through the communication network.

The control means may also be adapted, in addition to the previous two steps, for:

reading in the storage device a subscription identification to a health service, associating the measured parameter, the captured imprint and subscription identification into a single message, and delivering the single message to the transmission device, which transmits to the server through the communication network.

The device for storing the connection parameters and the subscription identification is for example a SIM card or a predetermined area in a data storage device of the medical device. The transmission device can be connected to the cable or wireless communication network. In the case of a wireless network, the transmission device can include, as the case may be and in a way known per se, a data transmission/reception antenna, and a modem: the modem is adapted for converting a data, a message or an instruction received from the control means into a format suitable for the communication network and for transmitting the converted data, message or instruction onto the antenna.

The control means can also be adapted for encrypting the message before transmission to the remote server. This prevents any malicious use of the single message.

The communication means can also comprise means for receiving a message validating the receipt sent by the remote server. The communication device can comprise in addition a device for storing the validation message, or a device for displaying said validation message, such as for example a display screen, an indicator light or means for displaying a sound signal (loudspeaker, . . . ); the control means is, as the case may be, adapted for storing the validation message in the storage device, or for displaying, on the display device, the validation message received from the remote server. The patient is thus informed that his data has been received by the remote server.

The control means can also be adapted to automatically re-activate the communication device in case of failure of a transmission of the measured parameter and the captured imprint to the remote server, several times if necessary, until receipt of the message of validation of receipt sent by the remote server.

The medical device according to the invention can also comprise a storage device, such as a rewritable memory and the control means is adapted for storing in the storage device the measured parameter and the captured imprint, or the single message, according to variants. Preferably, the control means is also adapted for deleting from the storage device the measured parameter and the captured imprint, or the single message, after transmission to the remote server. Thus, after transmission, the confidential information cannot be used.

The connection parameters correspond to a subscription to the telephone network used for data transfer; they are provided by the manager of the communication network. The subscription identification is an identification delivered to the patient (or to the healthcare professional providing the medical device to the patient) when subscribing to a health service managing the use of medical devices according to the invention; the subscription identification is for example recorded by a healthcare professional in the storage device (e.g. a SIM card.) of the medical device according to the invention during the supply of the medical device to the patient; in parallel, the healthcare professional, who assigns the medical device to the patient transmits to the medical healthcare service manager various information such as: an identification of the medical device delivered to the patient, an identification of the patient or parameters that identify the patient in a unique way (name, address, etc.), an imprint (of the type corresponding to those likely to be captured by the medical device) of the patient, an identification of the healthcare professional assigning the medical device to the patient, an identification of the healthcare professionals authorized to access the information regarding the patient on the databases of the healthcare service manager, etc.

BRIEF DESCRIPTION OF THE FIGURES

The invention will be better understood and further features and advantages of the invention will become clear from the following description of an exemplary embodiment of a medical device according to the invention, which example is given in a non-restrictive way. The description should be read together with the attached drawings, in which.

DESCRIPTION OF AN EMBODIMENT OF THE INVENTION

Figure 1:
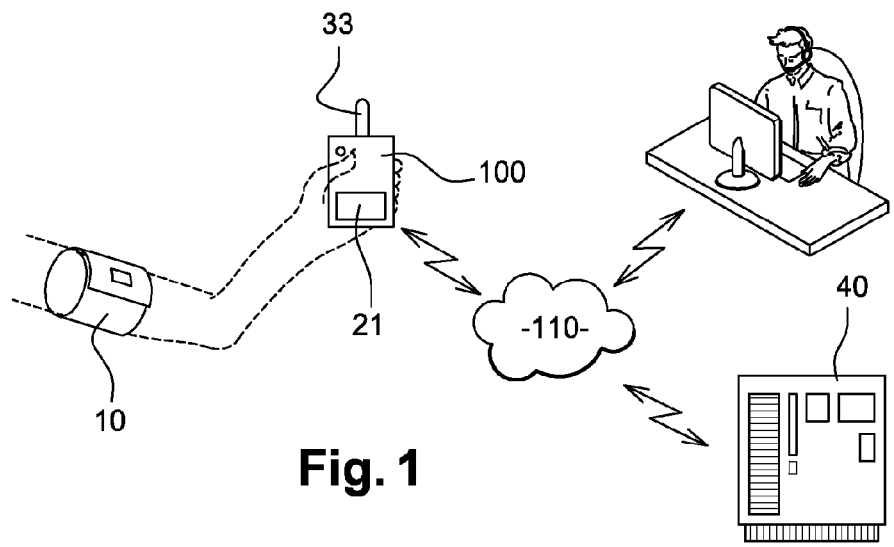
FIG. 1 shows a diagram of the use of a medical device according to the invention.
Figure 2:
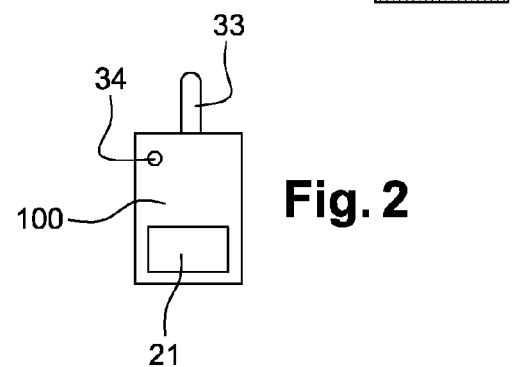
FIG. 2 is an external view of part of a device according to the invention, and FIG. 3 details the control box of a device according to the invention.

As stated above, a medical device according to the invention comprises one or several devices for measuring a health parameter of a patient, a device for capturing an imprint 20 identifying the patient, a device for communicating 30 with a remote server 40 and a control means 50.

The device for capturing an imprint 20, the communication device 30 and the control means 50 are, in the example shown, grouped together in one single control box 100, which can be of a small size, for example the size of a mobile phone or a digital tablet.

Figure 3:
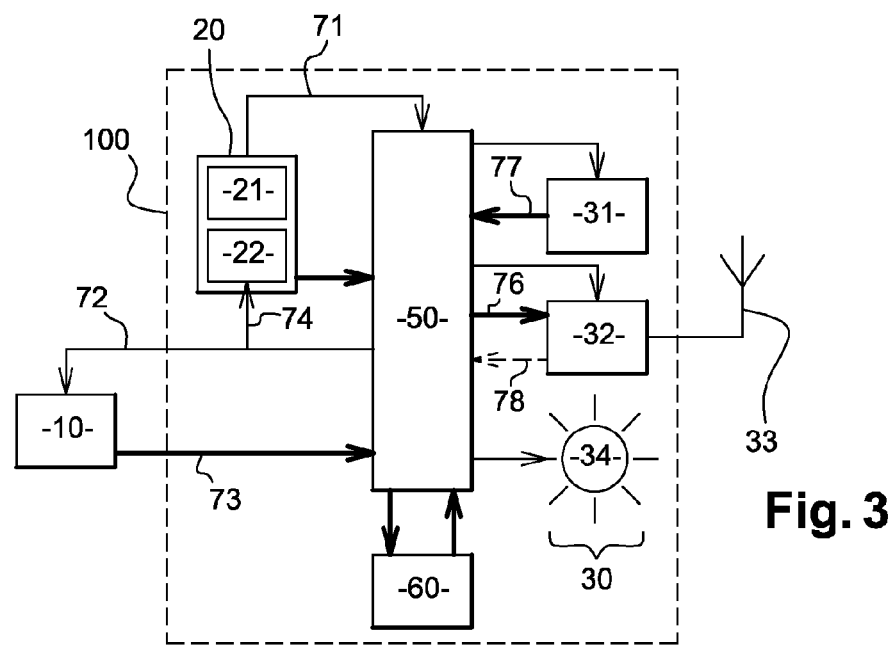

In FIG. 3 the main components integrated in the control unit are detailed. The thin line arrows indicate the direction of transmission between two components, and the thick line arrows indicate the direction of data transmission between two components.

In the example shown, the measuring device is a blood pressure gauge comprising namely a cuff 10 aimed at being placed on the arm of a patient and, in the control box 50, the control means 50 is connected to the cuff 10. In another example, not shown, the medical device is for example a chair on which the patient can sit, which chair integrates several measuring means, e.g. a weight measuring device, a casing for taking blood and analyzing determined blood parameters such, such as for example a level of creatinine, a temperature measuring device positioned at the level of a resting zone for the head of the patient on the back of the chair, etc. The box for controlling the assembly is positioned on an arm of the chair, so as to be manually accessible by the patient.

Depending on the size and shape of the measuring means, the measuring means can be in the same control box 100, or can be outside the box, connected to the control means by a cable or wireless connection, permitting the exchange of digital data (activation instructions and measurement results, etc.).

In the example shown, the means for capturing an imprint 20 is a means for capturing a fingerprint comprising a touch screen 21 and a copying means adapted for capturing an image of the touch screen 21. When the patient positions a finger on the touch screen 21, the touch screen activates the control means 50, which immediately activates the means for copying the imprint of the finger on the touch screen 21.

The measuring means provide the measured parameter in the form of a digital signal, which can be used directly by the communication means. In the same way, the means for capturing an imprint provides an imprint in the form of a digital signal, which can be used by the communication means.

When it activated by the patient (arrow 71), the control means 50 of the medical device according to the invention is arranged for:

activating the measuring device 10 (arrow 72) and obtaining in return a measured parameter (arrow 73), in the example a value of the blood pressure of the patient activating the device for capturing an imprint 20 (arrow 74) and obtaining in return an imprint (arrow 75), then, providing the measured parameter and the captured imprint to the communication device 30 (76) for transmission of the measured parameter and the captured imprint to the remote server 40.

In the example shown, the communication device 30 comprises, in turn, a storage device 31, a transmission device, a receiving device and a display device 34, driven by the control means 50 as follows:

the control means reads from the storage device 31 a connection parameter (arrow 77) and provides the connection parameter and a request for connection to the transmission device, which transmits to the communication network 110, the control means associates the measured parameter and the captured imprint in one single message, encrypts the single message and provides the encrypted message to the transmission device, which transmits to the server 40 through the communication network 110 the receiving device 40 receives from the remote server a message for validating the receipt (arrow 78), and the control means 50 transmits the received validation message to the display device 34, which displays it.

In the example shown, the storage device 31 is for example a SIM card, which contains identification parameters of the subscriber to a communication network, such as a telephone network or a network such as Internet. The transmission device and the receiving device include together an antenna 32 and a modem 33. The display device 34 is an indicator light, which displays for example a red color after activation of the medical device and until receiving the validation message and then displays a green color after receiving the validation message.

The measured parameter and the captured imprint can be associated by a simple adjoining (end to end) of the two digital signals, by a modulation with each other, or by any desired mathematical combination known in the field of digital signal processing.

In the example shown, the medical device also comprises a storage device 60, such as a writable memory. The control device 50 is adapted for storing in the storage device 60 the single message, then for deleting from the storage device the single message after transmission of the measured parameter and the captured imprint, or the single message at the remote server.

NOMENCLATURE 10 measuring device
20 imprint capturing device
   21 touch screen
30 communication device
   31 storage device
   32 modem
   33 antenna
   34 indicator light
40 remote server
50 control means
60 storage device
100 control box
110 communication network

What is claimed:

1. A medical device, comprising:
a control means activated by a single action of a patient;
a device for measuring a health parameter of a patient, said device for measuring being in communication with said control means, wherein said device for measuring communicates a measured health parameter according to said control means;

a device for capturing an imprint identifying the patient, said device for capturing being in communication with said control means, wherein said device for capturing communicates an identified imprint according to said control means;

a remote server having a database of identified imprints corresponding to patients and a database of pre-determined ranges of health parameters corresponding to said patients; and a device for communicating with said remote server, said device for communicating being in communication with said control means, wherein said device for communicating transmits said measured health parameter and said identified imprint to said remote server according to said control means, wherein said device for communicating transmits a confirmation response from said remote server to said control means, when said identified imprint matches at least one identified imprint in said database of identified imprints, wherein said device for communicating transmits an alert response from said remote server to said control means, when said identified imprint fails to match at least one identified imprint in said database of identified imprints, wherein said device for communicating transmits a validation response from said remote server to said control means, when said identified imprint matches at least one identified imprint in said database of identified imprints for one patient and when said measured health parameter falls within a pre-determined range of said health parameters corresponding to said one patient, and wherein said device for communicating transmits a warning response from said remote server to said control means, when said identified imprint matches at least one identified imprint in said database of identified imprints for one patient and when said measured health parameter fails to fall within a pre-determined range of said health parameters corresponding to said one patient.

2. The medical device, according to claim 1, wherein said device for measuring communicates a measured health parameter and said device for capturing communicates an identified imprint simultaneously according to said control means.

3. The medical device, according to claim 1, wherein said health parameter is selected from at least one of a group consisting of: weight of the patient, blood pressure of the patient, a level of creatinine in blood of the patient, a level of blood glucose in the blood of the patient, a level of prothrombin in the blood of the patient, a temperature of the patient, and a heart rate of the patient.

4. The medical device, according to claim 1, wherein said imprint is selected from at least one of a group consisting of: a fingerprint, an imprint of an eye, and an imprint of a face of the patient.

5. The medical device according to claim 1,
wherein said imprint is comprised of a fingerprint, said device for capturing comprising a touch screen, said medical device further comprising:
a copying means for said imprint, said copying means being in communication with said control means, said copying means capturing an image of said imprint on said touch screen according to said control means,
wherein said device for capturing communicates an identified imprint according to said control means, when a finger is detected on said touch screen.

6. The medical device of claim 1, wherein the device for communicating comprises:
a device for storing a said measured health parameter; and
a transmission device in communication with said device for storing and a communication network connected to said remote server,
wherein said device for communicating transmits a stored measured health parameter to said remote server through said communication network according to said control means,
wherein said device for communicating transmits said identified imprint to said remote server through said communication network with said stored measured health parameter according to said control means.

7. The medical device, according to claim 6, wherein said device for storing comprises a database of subscription identifications to a health service, and wherein said device for communicating transmits a subscription identification and said identified imprint to said remote server through said communication network with said stored measured health parameter according to said control means.

8. The medical device according to claim 7, wherein said device for communicating transmits a subscription identification and said identified imprint to said remote server through said communication network with said stored measured health parameter according to said control means with encryption.

9. The medical device, according to claim 7, wherein the device for communicating further comprises means for receiving, wherein said means for receiving communicates at least one response of a group consisting of: said confirmation response, said alert response, said validation response, and said warning response to said control means.

10. The medical device, according to claim 9, further comprising also a display device, said display device being selected from at least one of a group consisting of: a display screen, an indicator light, and a means for displaying a sound message, wherein said display device is in communication with said means for receiving, said at least one response being displayed on said display device.

11. The medical device, according to claim 1, further comprising: a storage device in communication with said control means, wherein at least one of said measured parameter and said identified imprint is stored in said storage device according to said control means.

12. The medical device, according to claim 11, wherein said at least one of said measured parameter and said identified imprint is deleted from said storage device according to said control means, after said device for communicating transmits said at least one of said measured parameter and said identified imprint.

* * * * *